United States Patent [19]

Dusza et al.

[11] 4,448,973

[45] May 15, 1984

[54] THERAPEUTICALLY ACTIVE 3-SUBSTITUTED AMINO-1-PHENYL AND SUBSTITUTED PHENYL-2-PYRAZOLINES

[75] Inventors: John P. Dusza, Nanuet, N.Y.; Joseph P. Joseph, Montvale, N.J.; Seymour Bernstein, New City, N.Y.

[73] Assignee: American Cyanamid Company, Stamford, Conn.

[21] Appl. No.: 376,885

[22] Filed: May 10, 1982

Related U.S. Application Data

[63] Continuation-in-part of Ser. No. 282,971, Jul. 13, 1981, abandoned.

[51] Int. Cl.$^3$ ............................................. C07D 231/06
[52] U.S. Cl. ................................. 548/362; 424/273 P
[58] Field of Search ........................................... 548/362

[56] References Cited

U.S. PATENT DOCUMENTS 2,726,248  12/1955  Kendall et al. ...................... 548/362
4,149,005   4/1979  Battisti et al. ....................... 548/362

OTHER PUBLICATIONS

Kost et al., Zhurnal Obshchey Khimii, 1959, vol. 29, No. 2, pp. 498–502.

*Primary Examiner*—Henry R. Jiles
*Assistant Examiner*—Kurt G. Briscoe
*Attorney, Agent, or Firm*—Anne M. Rosenblum

[57] ABSTRACT

3-substituted amino-1-phenyl-2-pyrazolines and 3-substituted amino-1-substituted phenyl-2-pyrazolines and their $C_4$ and $C_5$ analogs, useful for meliorating the inflammation and/or the progressive joint deterioration characteristic of arthritic disease, preventing the onset of asthmatic symptoms and allergic diseases, or as analgesic, antibacterial or antifungal agents.

4 Claims, No Drawings

THERAPEUTICALLY ACTIVE 3-SUBSTITUTED AMINO-1-PHENYL AND SUBSTITUTED PHENYL-2-PYRAZOLINES

This application is a continuation-in-part of our co-pending application, Ser. No. 282,971, filed July 13, 1981, now abandoned.

PRIOR ART

1. R. Battisti, et. al., U.S. Pat. No. 4,149,005 (Apr. 10, 1979) discloses compounds of the formula:

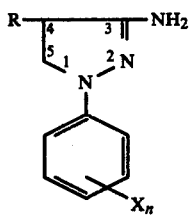

where R is H or $CH_3$, X is H, Br, Cl, alkyl, alkoxy or carboxyalkyl groups with from 1 to 4 carbon atoms or $CF_3$; and n is 1 or 2. These are disclosed as being used as intermediates in the preparation of 1-phenyl-3-aminopyrazoles as coupling components in azo dye manufacture. Related foreign patents: Ger. Offen. No. 2,727,706; French Pat. No. 2,355,834; Gr. Br. Pat. No. 1,515,500; Belgium Pat. No. 855,944; Netherland Pat. No. 7,706,760 and Japan Pat. No. 28,168.

2. G. A. Higgs, et. al., (Wellcome Research Laboratories); Biochemical Pharmacology, 28 1959 (1979) discloses 3-amino-1-[m-(trifluoromethyl)phenyl]-2-pyrazoline (BW 755C);

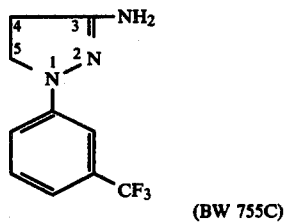

(BW 755C)

This compound is reported to have anti-inflammatory activity.

BRIEF SUMMARY OF THE INVENTION

This invention relates to new organic compounds and more particularly is concerned with novel 3-substituted amino-1-phenyl-2-pyrazolines and 3-substituted amino-1-substituted phenyl-2-pyrazolines and their $C_4$ and $C_5$ analogs which are represented by the following general formula:

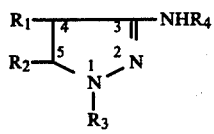

wherein $R_1$ and $R_2$ may be hydrogen or lower alkyl $(C_1-C_4)$; $R_3$ is

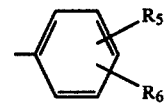

where $R_5$ and $R_6$ may be hydrogen, chloro or fluoro; $R_4$ is alkyl $(C_1-C_4)$, $CH_2CF_3$ or

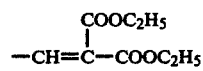

and the pharmacologically acceptable acid-addition salts thereof.

DETAILED DESCRIPTION OF THE INVENTION

The novel compounds of the present invention are generally obtainable as white to pale yellow crystalline solids having characteristic melting points and absorption spectra. The bases are appreciably soluble in solvents such as acetone, ethanol, toluene, methylene chloride and the like but are relatively insoluble in water. The organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

Preparation of the novel 3-substituted amino-1-phenyl-2-pyrazoline and 3-substituted amino-1-substituted phenyl-2-pyrazoline compounds V of the instant invention, which exhibit the pharmaceutical activity as herein described, is accomplished by the adaptation of the procedure of Duffin, G. F. and Kendall, J. D., J. Chem. Soc., 1954, 408; with modifications in accordance with the following reaction scheme:

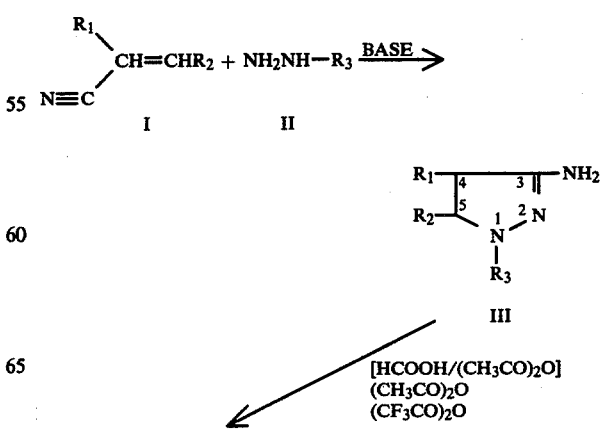

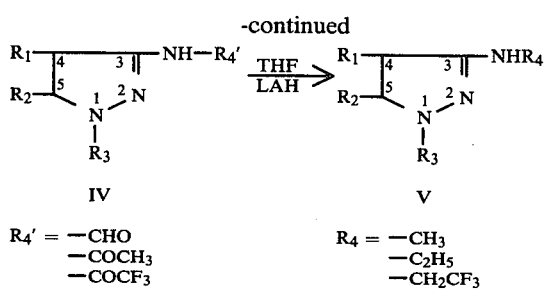

R4' = —CHO
—COCH3
—COCF3

R4 = —CH3
—C2H5
—CH2CF3 wherein $R_1$, $R_2$ and $R_3$ are as previously defined. In accordance with the above reaction scheme, phenylhydrazine or a halogen-mono or disubstituted phenylhydrazine hydrochloride II such as p-chlorophenylhydrazine hydrochloride, m-chlorophenylhydrazine hydrochloride, m-fluorophenylhydrazine hydrochloride or 3,4-dichlorophenylhydrazine hydrochloride is reacted with an $\alpha$, $\beta$-unsaturated nitrile I, such as acrylonitrile, methacrylonitrile, crotononitrile, cinnamonitrile, butyl acrylonitrile or compounds such as $\beta$-ethoxypropionitrile (which can undergo base catalyzed elimination to yield I) in a base catalyzed condensation procedure, with a base such as sodium ethoxide or choline hydrate in absolute ethanol. The reaction mixture is refluxed for a period of from 2–18 hours then the solvent is removed in vacuo. The addition of water gives a filterable solid which is collected, dissolved in dichloromethane and passed through a short column of a hydrous magnesium silicate. The column effluent is then refluxed on a steam bath with the gradual addition of hexane until crystallization is noted. Recrystallization from the same solvent pair (with or without additional treatment with a hydrous magnesium silicate) or from acetone-hexane provides the 3-amino-1-phenyl-2-pyrazoline and 3-amino-1-mono and disubstituted phenyl-2-pyrazoline compounds III. If the pyrazoline III is not soluble in dichloromethane, recrystallization may be accomplished from acetone-hexane, 95% ethanol or benzene with the omission of the hydrous magnesium silicate treatment phase.

The pyrazoline compound III is subjected to N-acylation by treating with an acylating agent such as a mixture of formic acid and acetic anhydride (Feiser and Feiser, Reagents for Organic Synthesis, Vol. 1, page 4), acetic anhydride, (with or without a catalyst such as 4-dimethylamino pyridine) or with trifluoroacetic anhydride at room temperature for 2–48 hours to yield the corresponding N-[1-phenyl-2-pyrazolin-3-yl]acetamide and N-[1-mono and disubstituted phenyl-2-pyrazolin-3-yl]acetamide, formamide and trifluoroacetamide derivatives IV which for the most part may be recrystallized from dichloromethane-hexane. The N-acylated compound IV is reduced under nitrogen with lithium aluminum hydride in freshly distilled tetrahydrofuran by refluxing for 4–7 hours. Then the excess hydride is cautiously decomposed with water and 15% aqueous sodium hydroxide and the mixture is filtered. The filtrate is evaporated and the residue is collected and purified in a conventional manner such as by recrystallization from hexane, passage through a hydrous magnesium silicate and recrystallization from a solvent such as hexane or a solvent pair such as dichloromethane-hexane and ether-hexane or by column chromatography on a synthetic magnesium silicate adsorbent and elution with acetone-hexane to give the novel 3-substituted amino-1-phenyl-2-pyrazoline and 3-substituted amino-1-substituted phenyl-2-pyrazoline compounds V of the instant invention.

The compounds of the present invention have utility as pharmacological agents. They are active either as anti-inflammatory agents, analgesic agents, antibacterial and/or antifungal agents and in many cases are active in more than one of these areas. Some of the compounds of this invention are further useful in inhibiting the progression of arthritis such as rheumatoid arthritis and inhibiting the progression of joint deterioration or preventing the onset of asthma and other allergic diseases. They also find utility in the amelioration or prevention of pathological reactions such as osteoarthritis, gout, acute synovitis and psoriasis.

Representative compounds of this invention have proven to be active in vivo as anti-inflammatory agents when tested by the Carrageenin Induced Edema of the Rat Paw Test. This test is a modification of the method of Winter, C. A., et al., Proc. Soc. Exp. Biol. and Med., 111, 544 (1962). Compounds found to be active in this test are:

1-(p-Chlorophenyl)-5-methyl-3-methylamino-2-pyrazoline
1-(3,4-Dichlorophenyl)-3-methylamino-2-pyrazoline
1-(p-Chlorophenyl)-4-methyl-3-methylamino-2-pyrazoline
1-(m-Chlorophenyl)-4-methyl-3-methylamino-2-pyrazoline
1-(p-Chlorophenyl)-5-methyl-3-(2,2,2-trifluoromethylamino)-2-pyrazoline
1-(p-Chlorophenyl)-4-methyl-3-[(2,2,2-trifluoroethyl)amino]-2-pyrazoline
1-(p-Chlorophenyl)-3-ethylamino-4-methyl-2-pyrazoline The compounds of the present invention also possess activity as analgesic agents. A method employed for measuring the in vivo activity of the compounds of the present invention is the "writhing syndrome" test for analgesic activity as described by Siegmund, et al., Proc. Soc. Exp. Biol. and Med., 05, 729 (1957), with modifications. Representative compounds of the present invention which are active when tested by the "writhing syndrome" test are listed below:

3-Ethylamino-1-(m-fluorophenyl)-4-methyl-2-pyrazoline
3-Ethylamino-4-methyl-1-phenyl-2-pyrazoline Representative compounds of the present invention have been proven active in vitro as antibacterial and/or antifungal agents when tested by such procedures as the standard agar dilution procedure. Compounds proven active in these tests include:

{{[1-(p-Chlorophenyl)-2-pyrazolin-3-yl]amino}methylene}malonic acid, diethyl ester
1-(p-Chlorophenyl)-5-methyl-3-methylamino-2-pyrazoline
1-(3,4-Dichlorophenyl)-3-methylamino-2-pyrazoline
1-(p-Chlorophenyl)-4-methyl-3-methylamino-2-pyrazoline
1-(m-Chlorophenyl)-4-methyl-3-methylamino-2-pyrazoline
1-(p-Chlorophenyl)-5-methyl-3-(2,2,2-trifluoroethylamino)-2-pyrazoline The compounds of the present invention have been found to be highly useful for the above pharmaceutical therapy, when administered in amounts ranging from about 0.5 milligram to about 250 mg. per kilogram of body weight per day. A preferred dosage regimen for optimum results would be from about 5 mg to about 100 mg per kilogram of body weight per day, and such dosage units are employed that a total of from about 0.35 g to about 7.0 g of the active ingredient for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, intraarticular, topical or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chloro-phenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The compounds of this invention are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

For the control of asthma or allergic responses, the active ingredient may also be administered by inhalation. For the inhalation routes, an inhaler device may be employed with the active ingredient in a suitable form such as powder or solution with appropriate pharmaceutical carriers.

This invention will be described in greater detail in conjunction with the following examples.

EXAMPLE 1

{{[1-(p-Chlorophenyl)-2-pyrazolin-3-yl]amino}methylene}malonic acid, diethyl ester (A) A 2.8 g. amount of sodium metal is dissolved in 200 ml. of absolute ethanol, then 17.9 g. of p-chlorophenylhydrazine hydrochloride is added followed in 25 minutes by 5.5 g. of acrylonitrile. The reaction mixture is refluxed for 6 hours and filtered while hot. The filtrate is evaporated to dryness then water is added to separate a solid. The solid is collected by filtration and dissolved in dichloromethane. This solution is passed through a short column of a hydrous magnesium silicate. The effluent is heated to boiling and hexane is added to crystallize a product. The mixture is cooled and filtered to give 8.75 g. of 3-amino-1-(p-chlorophenyl)-2-pyrazoline as colorless needles, m.p. 142.5°–145° C.

(B) A mixture of 3.90 g. of the preceding product and 4.32 g. of ethoxymethylenediethylmalonate is heated at reflux for 2 hours then the solution is evaporated to dryness to give a solid. The solid is dissolved in methylene chloride and treated with a hydrous magnesium silicate and hexane as previously described to collect a solid. The solid is recrystallized from acetone-hexane to give 4.78 g. of the product of the Example as yellow prisms, m.p. 159°–162° C.

EXAMPLE 2

1-(p-Chlorophenyl)-5-methyl-3-methylamino-2-pyrazoline (A) A 1.72 g. amount of sodium metal is dissolved in 110 ml. of absolute ethanol, then 11.0 g. of p-chlorophenylhydrazine hydrochloride is added followed in 15 minutes by 4.20 g. of crotononitrile. The reaction mixture is refluxed for 18 hours. The solvent is removed in vacuo and water is added to the residue to separate a gum. The gum is dissolved in dichloromethane and separated from the aqueous layer. The organic layer is dried over anhydrous magnesium sulfate and filtered through a short column of a hydrous magnesium silicate. The effluent is evaporated to give a glass. A small amount of benzene and then hexane is added to the glass which gradually solidifies. The solid is collected, washed with hexane and dried to give 8.1 g. of 3-amino-1-(p-chlorophenyl)-5-methyl-2-pyrazoline as a pink solid, m.p. 90°–92° C.

(B) A 4.8 g. amount of the preceding compound is dissolved in 25 ml. of a mixture of formic acid and acetic anhydride (Feiser and Feiser, Reagents for Organic Synthesis, Vol. 1, page 4) and allowed to remain at room temperature for 3 hours. Then ice water is added to the mixture to give a gum. The aqueous phase is decanted and the gum is dissolved in dichloromethane. The solution is dried over magnesium sulfate, filtered through a hydrous magnesium silicate and evaporated leaving a yellow gum. This material is dissolved in dichloromethane and heated to boiling, then hexane is added until turbidity occurs. The mixture is cooled and filtered to yield 3.6 g. of N-[1-(p-chlorophenyl)-5-methyl-2-pyrazolin-3-yl]formamide as off-white crystals, m.p. 112°–113° C.

(C) To a stirred solution of 250 ml. of freshly distilled tetrahydrofuran under nitrogen is added cautiously 3.3 g. of lithium aluminum hydride, then 3.3 g. of N-[1-(p-chlorophenyl)-5-methyl-2-pyrazolin-3-yl]formamide is added and the mixture is refluxed under nitrogen for 4 hours. The reaction mixture is cooled. Then with stirring, 3.3 ml. of water is cautiously added dropwise, followed by 3.3 ml. of 15% aqueous sodium hydroxide solution and 10.0 ml. of water. The mixture is filtered and the residue is washed with ether. The combined filtrate and wash is evaporated to dryness giving a gum which solidifies. The solid is collected, washed with hexane and dried. The product of the Example is recrystallized from dichloromethane-hexane to give 2.3 g. of white crystals, m.p. 102°–103° C.

EXAMPLE 3

1-(3,4-Dichlorophenyl)-3-methylamino-2-pyrazoline (A) A 9.9 g. amount of sodium metal is dissolved in 450 ml. of absolute ethanol, then 75.0 g. of 3,4-dichlorophenylhydrazine hydrochloride is added, followed in 10 minutes by 19.5 g. of acrylonitrile. The reaction mixture is refluxed for 18 hours then the solvent is removed in vacuo. Water is added to the residue to separate a granular solid. The solid is collected by filtration and dissolved in acetone. This solution is filtered and the filtrate is evaporated to dryness. The resulting residue is triturated with ether to give 62.4 g. of 3-amino-1-(3,4-dichlorophenyl)-2-pyrazoline as a tan crystalline solid, m.p. 181°–183° C.

(B) A 10.0 g. amount of the preceding product is dissolved in 50 ml. of a mixture of formic acid and acetic anhydride (Feiser and Feiser, Reagents for Organic Synthesis, Vol. 1, page 4) and allowed to remain at room temperature for 2 hours. The resulting solid is collected by filtration and dissolved in dichloromethane. The organic solution is washed with water, dried over anhydrous magnesium sulfate and filtered through a short column of a hydrous magnesium silicate. The effluent is concentrated, adding hexane until turbidity occurs. The mixture is cooled and filtered to give 6.5 g. of N-[1-(3,4-dichlorophenyl)-3-pyrazolin-3-yl]formamide as a white solid, m.p. 148°–149° C.

(C) To a stirred solution of 250 ml. of freshly distilled tetrahydrofuran under nitrogen is added cautiously 5.0 g. of lithium aluminum hydride, then 5.0 g. of N-[1-(3,4-dichlorophenyl)-3-pyrazolin-3-yl]formamide is added portionwise and the mixture is refluxed under nitrogen for 6 hours. The reaction mixture is cooled and the excess hydride is decomposed by the cautious dropwise addition of 5.0 ml. of water followed by 5.0 ml. of 15% sodium hydroxide solution and 15 ml. of water. The mixture is filtered and the filtrate is evaporated to give a gum and solid. This material is dissolved in dichloromethane and passed through a short column of a hydrous magnesium silicate. The effluent is evaporated to give a dark gum and solid. The mixture is dissolved in ether and treated as above with a hydrous magnesium silicate. The effluent is evaporated and the solid is recrystallized twice from ether-hexane to give 2.0 g. of the desired product as white crystals, m.p. 68°–70° C.

EXAMPLE 4

1-(p-Chlorophenyl)-4-methyl-3-methylamino-2-pyrazoline (A) A 1.2 g. amount of sodium metal is dissolved in 110 ml. of absolute ethanol, then 7.5 g. of p-chlorophenylhydrazine hydrochloride is added followed by 2.9 g. of methacrylonitrile. The reaction mixture is refluxed for 18 hours. The solvent is removed in vacuo and water is added to the residue to separate a gum. The gum is collected and dissolved in dichloromethane. The organic solution is washed with water, dried over anhydrous magnesium sulfate and filtered through a short column of a hydrous magnesium silicate. The effluent is evaporated leaving a gum which solidifies upon adding hexane. The solid is collected and recrystallized from ether-hexane to give 4.6 g. of 3-amino-1-(p-chlorophenyl)-4-methyl-2-pyrazoline as white crystals, m.p. 107°–108° C.

(B) A 2.2 g. amount of the preceding product is dissolved in 10.0 ml. of a mixture of formic acid and acetic anhydride [Example 3 (B)]. The mixture is allowed to remain at room temperature for 3 hours. Water is added and a yellow solid is collected by filtration. The solid is dissolved in dichloromethane. The solution is dried, filtered and concentrated as described in Example 3 (B) to give 2.1 g. of N-[1-(p-chlorophenyl)-4-methyl-2-pyrazolin-3-yl]formamide as a white solid, m.p. 172°–174° C.

(C) A 1.9 g. amount of the preceding product is added to a suspension of 1.9 g. of lithium aluminum hydride in 100 ml. of freshly distilled tetrahydrofuran under nitrogen and refluxed for 4 hours as described in Example 3 (C). The reaction mixture is cooled and the excess hydride is decomposed as previously described with water and 15% sodium hydroxide. The mixture is filtered and the filtrate is evaporated. The residue is dissolved in dichloromethane and the solution is passed through a short column of a hydrous magnesium silicate. The effluent is evaporated in vacuo to give a cloudy gum. The gum is dissolved in ether and filtered. The filtrate is evaporated in vacuo and cooled. The addition of hexane provides crystals. The crystals are collected and dissolved in ether. The solution is filtered then hexane is added until turbidity appears. The solution is cooled and seeded to yield 1.18 g. of the product of the Example as white crystals m.p. 70°-72° C.

EXAMPLE 5

1-(m-Chlorophenyl)-4-methyl-3-methylamino-2-pyrazoline (A) A 3.12 g. amount of sodium metal is dissolved in 200 ml. of absolute ethanol, then 20.9 g. of m-chlorophenylhydrazine hydrochloride is added, followed by 7.6 g. of methacrylonitrile. The reaction mixture is refluxed, extracted and filtered as for Example 4 (A) to give a solid. The solid is recrystallized twice from ether-hexane to give 16.2 g. of 3-amino-1-(m-chlorophenyl)-4-methyl-2-pyrazoline as white crystals, m.p. 84°-85° C.

(B) A 3.0 g. amount of the preceding product is dissolved in 10 ml. of a mixture of formic acid and acetic anhydride [Example 3 (B)] and is allowed to remain at room temperature for 3 hours. The reaction mixture is then poured into water to separate a partial gum and solid. This material is collected, dissolved in dichloromethane and filtered through a short column of a hydrous magnesium silicate. The effluent is concentrated while adding hexane to separate 3.1 g. of N-[1-(m-chlorophenyl)-4-methyl-2-pyrazolin-3-yl]formamide as light yellow crystals, m.p. 140°-142° C.

(C) As for Example 3 (C), a 2.0 g. amount of the preceding compound is added to a suspension of 2.0 g. of lithium aluminum hydride in 200 ml. of freshly distilled tetrahydrofuran under nitrogen and refluxed for 4 hours. The reaction mixture is cooled and the excess hydride is decomposed and treated as described in Example 3 (C) to give a solid. The solid is recrystallized from ether-hexane to give 1.3 g. of crude product. A 200 mg. amount of this material is recrystallized twice more from ether-hexane after filtration through diatomaceous earth to give 100 mg. of the desired product as white crystals, m.p. 75°-76° C.

EXAMPLE 6

1-(p-Chlorophenyl)-5-methyl-3-(2,2,2-trifluoroethylamino)-2-pyrazoline (A) A 8.0 g. amount of 3-amino-1-(p-chlorophenyl)-5-methyl-2-pyrazoline [prepared as described in Example 2 (A)] is dissolved in 25.0 ml. of dichloromethane with stirring. This solution is slowly added with stirring to 25.0 ml. of trifluoroacetic anhydride cooled at 10° C. The reaction mixture is stirred for 3 hours at room temperature then the solvent is removed in vacuo. The residue is dissolved in dichloromethane and this solution is passed through a short column of a hydrous magnesium silicate. The effluent is concentrated while adding hexane until turbidity results. The solution is cooled, then filtered to give 8.5 g. of N-[1-(p-chlorophenyl)-5-methyl-2-pyrazolin-3-yl]-2,2,2-trifluoroacetamide as a white solid, m.p. 170°-172° C.

(B) To a stirred solution of 250 ml. of freshly distilled tetrahydrofuran under nitrogen is added cautiously 5.0 g. of lithium aluminum hydride, then 5.0 g. of the above product is added portionwise to the mixture. The reaction mixture is stirred under nitrogen and refluxed for 7 hours. The reaction mixture is cooled and the excess hydride is decomposed by the cautious dropwise addition of 5.0 ml. of water followed by 5.0 ml. of 15% sodium hydroxide solution and 15 ml. of water. The mixture is filtered and the filtrate is evaporated leaving a thin oil. The oil is dissolved in dichloromethane. This solution is dried over anhydrous magnesium sulfate, passed through a hydrous magnesium silicate and evaporated to give a gum which solidifies when triturated with hexane. The solid is recrystallized from dichloromethane-hexane to give 2.8 g. of the product of the Example as white crystals, m.p. 63°-64° C.

EXAMPLE 7

1-(p-Chlorophenyl)-4-methyl-3-[(2,2,2-trifluoroethyl)amino]-2-pyrazoline (A) A 7.0 g. amount of 3-amino-1-(p-chlorophenyl)-4-methyl-2-pyrazoline [prepared as described in Example 4 (A)] is dissolved in 25.0 ml. of dichloromethane and cooled to 5° C. The solution is stirred and 14.0 ml. of trifluoroacetic anhydride is added. Stirring is continued at room temperature for 3 hours, then the solvent is removed in vacuo. The residue is dissolved in dichloromethane and the solution is concentrated with the addition of hexane until turbidity appears. The mixture is cooled and the solid is collected to give 5.3 g. of product. A 1.0 g. amount of this material is recrystallized from dichloromethane-hexane to give 750 mg. of N-[1-(p-chlorophenyl)-4-methyl-2-pyrazolin-3-yl]-2,2,2-trifluoroacetamide as a white solid, m.p. 181°-183° C.

(B) To a stirred solution of 400 ml. of freshly distilled tetrahydrofuran under nitrogen is added cautiously 6.9 g. of lithium aluminum hydride, then 6.9 g. of the preceding product (prepared as described above) is added portionwise to the mixture. The reaction mixture is stirred under nitrogen and refluxed for 5 hours. The reaction mixture is cooled and the excess hydride is decomposed by the cautious dropwise addition of 6.9 ml. of water followed by 6.9 ml. of 15% sodium hydroxide solution and 20.7 ml of water. The mixture is filtered and the filtrate is evaporated leaving a crude tacky tan solid. The solid is dissolved in ether and filtered through a micronized synthetic magnesium silicate adsorbent. The effluent is concentrated while adding hexane until turbidity occurs. The mixture is cooled in a refrigerator then filtered to give 3.4 g. of the desired product as a white solid, m.p. 84°-86° C.

EXAMPLE 8

1-(p-Chlorophenyl)-3-ethylamino-5-methyl-2-pyrazoline

A mixture of 8.0 g. of 3-amino-1-(p-chlorophenyl)-5-methyl-2-pyrazoline [prepared as described in Example 2 (A)], 400 mg. of 4-dimethylamino pyridine and 20.0 ml. of acetic anhydride is allowed to stand at room temperature for 48 hours. The solid formed is collected by filtration, washed with cold acetic anhydride then with hexane and is dried to give a white solid. The solid is recrystallized from dichloromethane-hexane to give 6.6 g. of N-[1-(p-chlorophenyl)-5-methyl-2-pyrazolin-3-yl]acetamide as a white solid, m.p. 167°-169° C.

To a stirred solution of 300 ml. of freshly distilled tetrahydrofuran under nitrogen is added cautiously 6.0 g. of lithium aluminum hydride, then 6.0 g. of the preceding product is added portionwise to the mixture. The reaction mixture is stirred under nitrogen and refluxed for 5 hours. The reaction mixture is cooled and the excess hydride is decomposed as described in Example 7 (B) using 6.0 ml. of water, 6.0 ml. of 15% sodium hydroxide solution and 18.0 ml. of water. The residual solid is filtered and washed with tetrahydrofuran. The combined filtrate and wash is evaporated to give a thin oil. The oil is dissolved in dichloromethane, filtered through a hydrous magnesium silicate and evaporated to again give a thin oil. The addition of hexane separates 4.7 g. of crystals. A 200 mg. amount of the solid is recrystallized from ether-hexane to give 138 mg. of the desired product as a white solid, m.p. 57°–58° C.

EXAMPLE 9

1-(p-Chlorophenyl)-3-ethylamino-4-methyl-2-pyrazoline (A) A 1.2 g. amount of sodium metal is dissolved in 110 ml. of absolute ethanol, then 7.5 g. of p-chlorophenylhydrazine hydrochloride is added followed by 2.9 g. of methacrylonitrile. The reaction mixture is refluxed for 18 hours. The procedure of Example 2 (A) is followed through the column filtration step. The effluent is evaporated leaving a gum which solidifies upon adding hexane. The solid is recrystallized from ether-hexane to give 4.6 g. of 3-amino-1-(p-chlorophenyl)-4-methyl-2-pyrazoline as white crystals, m.p. 107°–108° C.

(B) A 9.0 g. amount of the preceding compound (prepared as described above) is dissolved in 54.0 ml. of acetic anhydride. The warm solution is allowed to stand for 16 hours at room temperature with some solid separation. Water is added to complete the solid separation. The solid is collected by filtration and is dissolved in methanol. Then 1 N potassium hydroxide in methanol is added to make basic. After 15 minutes at room temperature the solvent is removed in vacuo and water is added to separate a solid. The solid is collected and recrystallized from dichloromethane-hexane to give 6.5 g. of N-[1-(p-chlorophenyl)-4-methyl-2-pyrazolin-3-yl]acetamide as white crystals, m.p. 172°–173° C.

(C) A 6.5 g. amount of the above compound is added to a stirred suspension under nitrogen of 6.5 g. of lithium aluminum hydride in 250 ml. of freshly distilled tetrahydrofuran. The stirred reaction mixture is refluxed for 5 hours under nitrogen. Then the mixture is cooled and the excess hydride is decomposed as described in Example 7 using 6.5 ml. of water, 6.5 ml. of 15% sodium hydroxide solution and 13 ml. of water. The residual solid is filtered and washed with tetrahydrofuran. The combined filtrate and wash is evaporated to a thin oil which crystallizes. The solid is collected and recrystallized from dichloromethane-hexane to give 4.6 g. of product. A 115 mg. amount of product is recrystallized from ether-hexane to give 90 mg. of the desired product as white crystals, m.p. 63°–64° C.

EXAMPLE 10

1-(3,4-Dichlorophenyl)-3-(2,2,2-trifluoroethylamino)-2-pyrazoline

A 10.0 g. amount of 3-amino-1-(3,4-dichlorophenyl)-2-pyrazoline [Example 3 (A)] is added portionwise with cooling and stirring to 50 ml. of trifluoroacetic anhydride with separation of a solid. The reaction mixture is stirred for 3 hours at room temperature then the solid is collected by filtration and dried to give 12.2 g. of product. A 3.0 g. amount of this material is recrystallized from dichloromethane-hexane to give 2.4 g. of N-[1-(3,4-dichlorophenyl)-2-pyrazolin-3-yl]-2,2,2-trifluoroacetamide as pale yellow needles, m.p. 163°–164° C.

A 5.0 g. portion of the above product is refluxed for 4 hours with lithium aluminum hydride in tetrahydrofuran as described in Example 6 (B). The hydride is decomposed as described and the reaction mixture is filtered. The filtrate is evaporated to give a dark gum. The gum is dissolved in dichloromethane and filtered through a hydrous magnesium silicate. The filtrate is evaporated to give a thin green oil which crystallizes on standing. This material is recrystallized twice with hexane to give 3.6 g. of the desired product as a grey solid, m.p. 93°–94° C.

EXAMPLE 11

3-Ethylamino-1-(m-fluorophenyl)-4-methyl-2-pyrazoline (A) A 2.8 g. amount of sodium metal is dissolved in 200 ml. of absolute ethanol, then 16.2 g. of m-fluorophenylhydrazine hydrochloride is added followed by 13.4 g. of methacrylonitrile. The reaction mixture is refluxed for 18 hours then the solvent is evaporated in vacuo. Water is added to give a gum. The gum is dissolved in dichloromethane and the solution is passed through a short column of a hydrous magnesium silicate. The effluent is concentrated while adding hexane until turbidity occurs. The solution is cooled and seeded to separate a pink solid which is collected by filtration and dried to give 4.2 g. of 3-amino-1-(m-fluorophenyl)-4-methyl-2-pyrazoline.

(B) A 4.2 g. amount of the preceding compound is dissolved in 10.0 ml. of acetic anhydride then 100 mg. of 4-dimethylamino pyridine is added and the reaction mixture is allowed to stand at room temperature for 16 hours. The mixture is poured into water to separate a gum which solidifies. The solid is collected by filtration and washed with water. The solid is dissolved in 50.0 ml. of methanol and 10.0 ml. of 1 N sodium hydroxide in methanol is added. The mixture is allowed to stand at room temperature for 30 minutes then the solvent is partly removed in vacuo. The addition of water separates a yellow solid. The solid is collected and dried to give 4.1 g. of N-[1-(m-fluorophenyl)-4-methyl-2-pyrazolin-3-yl]acetamide, m.p. 171°–172° C.

(C) A 4.5 g. amount of the preceding compound (prepared as described above) is added to a stirred suspension under nitrogen of 4.5 g. of lithium aluminum hydride in 250 ml. of freshly distilled tetrahydrofuran. The reaction mixture is stirred and refluxed for 5 hours under nitrogen. The mixture is cooled and the excess hydride is decomposed as described in Example 7 (B) using 4.5 ml. of water, 4.5 ml. of 15% sodium hydroxide solution and 14 ml. of water. The mixture is filtered and the filtrate is evaporated in vacuo to give a gum. The gum is placed on a column containing 80 g. of a synthetic magnesium silicate adsorbent. The column is eluted first with hexane (cuts 1 and 2), then with 2% acetone-hexane (cuts 3 and 4 combined and cuts 5, 6 and 7 combined), then with 4% acetone-hexane (cuts 8, 9 and 10 combined). The elution procedure is monitored by thin layer chromatography using the upper phase of a mixture of 2 parts benzene, 1 part acetone and 2 parts water to develop the plate. The fraction represented by combining cuts 5, 6 and 7 is evaporated to give 0.9 g. of the desired product as a pink oil.

EXAMPLE 12

3-Ethylamino-4-methyl-1-phenyl-2-pyrazoline

A 2.0 g. amount of sodium metal is dissolved in 200 ml. of absolute ethanol, then 37.4 g. of phenylhydrazine is added followed in 10 minutes by 20.1 g. of methacrylonitrile. The reaction mixture is refluxed for 4 hours then is evaporated to near dryness in vacuo. Water is added to the residue to separate an oil. The oil crystallizes on standing. The solid is dissolved in dichloromethane. The solution is passed through a short column of a hydrous magnesium silicate. The column effluent is evaporated to give an oil. The oil is crystallized from acetone-hexane then is recrystallized from the same solvent pair to give 20.88 g. of 3-amino-4-methyl-1-phenyl-2-pyrazoline as colorless crystals, m.p. 83°–84° C.

A 10.0 g. amount of the preceding product is dissolved in 50 ml. of acetic anhydride, then 500 mg. of 4-dimethylaminopyridine is added and the reaction mixture is allowed to stand at room temperature for 18 hours. The mixture is poured into water to separate a gum which solidifies and is collected by filtration. The solid is added with stirring to 150 ml. of methanol containing 10.0 g. of sodium hydroxide. After 30 minutes the solvent is removed in vacuo and water is added to provide a gum which becomes solid. This solid is dissolved in dichloromethane, dried over anhydrous magnesium sulfate and passed through a short column of a hydrous magnesium silicate. The effluent is concentrated while adding hexane to yield crystals. The material is collected and dried to give 3.3 g. of N-(4-methyl-1-phenyl-2-pyrazolin-3-yl)acetamide as a white solid, m.p. 149°–150° C.

A 6.0 g. amount of the preceding compound (prepared as described above) is added to a stirred suspension under nitrogen of 6.0 g. of lithium aluminum hydride in 250 ml. of freshly distilled tetrahydrofuran. The reaction mixture is stirred and refluxed for 5 hours under nitrogen. The mixture is cooled and the excess hydride is decomposed as described in Example 7 (B) using 6.0 ml. of water, 6.0 ml. of 15% sodium hydroxide solution and 18 ml. of water. The mixture is filtered and the filtrate is evaporated in vacuo to give an oil. The oil is placed on a column containing 80 g. of a 200 mesh synthetic magnesium silicate adsorbent. The column is eluted first with 2% acetone hexane (cut 1), then with 4% acetone-hexane (cuts 2, 3, 4, 5 and 6) and finally with 8% acetone-hexane (cut 7). The elution procedure is monitored by thin layer chromatography using the system described in Example 11 (C). The fraction represented by combining cuts 2, 3, 4, 5 and 6 is evaporated to give 4.3 g. of the desired product as a pink oil.

EXAMPLE 13

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| Magnesium Stearate USP | 0.1–5.0 (% w/w) |

EXAMPLE 14

| Preparation of Compressed Tablet | |
|---|---|
| Ingredient | mg./tablet |
| Active Compound | 0.5–500 |
| Dibasic Calcium Phosphate N.F. | qs |
| Starch USP | 40 |
| Modified Starch | 10 |
| *Surfactant, e.g. Sodium Lauryl Sulfate | 0.1–2.0 (% w/w) |
| Magnesium Stearate USP | 0.1–5.0 (% w/w) |

*Other surface active agents such as disodium sulfosuccinate and nonionic surface active agents such as Span ® and Tween ® may also be employed.

EXAMPLE 15

| Preparation of Compressed Tablet | |
|---|---|
| Ingredient | mg./tablet |
| Active Compound | 0.5–500 |
| Direct Compression Sugar Agent e.g. Emdex | qs |
| Magnesium Stearate | 0.1–3.0 (% w/w) |

EXAMPLE 16

| Preparation of Hard Shell Capsule | |
|---|---|
| Ingredient | mg./capsule |
| Active Compound | 0.5–500 |
| Lactose, Spray Dried | qs |
| Magnesium Stearate | 0.1–3.0 (% w/w) |

EXAMPLE 17

| Preparation of Oral Liquid (Syrup) | |
|---|---|
| Ingredient | % w/v |
| Active Compound | 0.05–5 |
| Liquid Sugar | 75.0 |
| Methyl Paraben USP | 0.18 |
| Propyl Paraben USP | 0.02 |
| Suspending Agent e.g. Avicel | 0.5–1.0 |
| Flavoring Agent | qs |
| Purified Water qs ad | 100.0 |

EXAMPLE 18

| Preparation of Oral Liquid (Elixir) | |
|---|---|
| Ingredient | % w/v |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 19

| Preparation of Oral Suspension (Syrup) | |
|---|---|
| Ingredient | % w/v |
| Active Compound | 0.05–5 |
| Polysorbate 80 USP | 0.1 |
| Magnesium Aluminum Silicate, Colloidal | 0.3 |

-continued

Preparation of Oral Suspension (Syrup)

| Ingredient | % w/v |
|---|---|
| Dye | 0.001–0.5 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 20

Preparation of Injectable Solution

| Ingredient | % w/v |
|---|---|
| Active Compound | 0.05–5 |
| Benzyl Alcohol N.F. | 0.9 |
| Water for Injection | 100.0 |

EXAMPLE 21

Preparation of Injectable Oil

| Ingredient | % w/v |
|---|---|
| Active Compound | 0.05–5 |
| Benzyl Alcohol | 1.5 |
| Sesame Oil qs ad | 100.0 |

EXAMPLE 22

Preparation of Intra-articular Product

| Ingredient | Amount |
|---|---|
| Active Compound | 2–20 mg. |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 23

Preparation of Injectable Depo Suspension

| Ingredient | % w/v |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 24

Preparation of Topical Cream

| Ingredient | % w/w |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 25

Preparation of Topical Ointment

| Ingredient | % w/w |
|---|---|
| Active Compound | 0.05–5 |
| Cholesterol | 3 |
| Stearyl Alcohol | 3 |
| White Wax | 8 |
| Petrolatum, White USP qs | 100 |

We claim:

1. A compound selected from the group consisting of those of the formula:

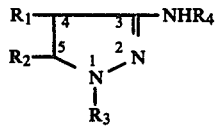

wherein $R_1$ and $R_2$ may be hydrogen or lower alkyl ($C_1$–$C_4$); $R_3$ is

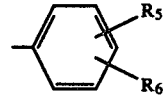

where $R_5$ and $R_6$ may be hydrogen, chloro or fluoro; $R_4$ is $CH_2CF_3$ or

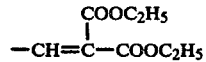

and the pharmacologically acceptable acid-addition salts thereof.

2. The compound according to claim 1, {{[1-(p-chlorophenyl)-2-pyrazolin-3-yl]amino}methylene}malonic acid, diethyl ester.

3. The compound according to claim 1, 1-(p-chlorophenyl)-5-methyl-3-(2,2,2-trifluoroethylamino)-2-pyrazoline.

4. The compound according to claim 1, 1-(p-chlorophenyl)-4-methyl-3-[(2,2,2-trifluoroethyl)amino]-2-pyrazoline.

* * * * *